United States Patent [19]

Yamaguchi et al.

[11] Patent Number: 5,186,808

[45] Date of Patent: Feb. 16, 1993

[54] FILM-COATED SENSOR

[75] Inventors: Shuichiro Yamaguchi; Naoto Uchida; Satoru Kasai; Takeshi Shimomura, all of Kanagawa; Noboru Oyama, Tokyo, all of Japan

[73] Assignee: Terumo Kabushiki Kaisha, Tokyo, Japan

[21] Appl. No.: 548,931

[22] PCT Filed: Jan. 27, 1989

[86] PCT No.: PCT/JP89/00085

§ 371 Date: Jul. 27, 1990

§ 102(e) Date: Jul. 27, 1990

[87] PCT Pub. No.: WO89/07262

PCT Pub. Date: Aug. 10, 1989

[30] Foreign Application Priority Data

Jan. 29, 1988 [JP] Japan ............... 63-017414
Apr. 4, 1988 [JP] Japan ............... 63-081419

[51] Int. Cl.$^5$ .............................. G01N 27/26
[52] U.S. Cl. .................... 204/418; 204/403; 204/415; 204/416
[58] Field of Search ........... 204/415, 418, 419, 403, 204/412, 424, 428, 426, 416

[56] References Cited

U.S. PATENT DOCUMENTS

| | | | |
|---|---|---|---|
| 3,476,670 | 11/1969 | Weiner | 204/418 |
| 4,132,616 | 1/1979 | Tantram et al. | 204/415 |
| 4,198,851 | 4/1980 | Janata | 73/23 |
| 4,545,382 | 10/1985 | Higgins et al. | 204/415 |
| 4,563,263 | 1/1986 | Oyama et al. | 204/418 |
| 4,615,954 | 10/1986 | Solomon et al. | 429/27 |
| 4,753,719 | 6/1988 | Yamaguchi et al. | 204/418 |
| 4,798,664 | 1/1989 | Yamaguchi et al. | 204/418 |
| 4,816,118 | 3/1989 | Oyama et al. | 204/418 |
| 4,839,020 | 6/1989 | Yamaguchi et al. | 204/431 |
| 4,861,454 | 8/1989 | Ushizawa et al. | 204/415 |
| 4,871,442 | 10/1989 | Yamaguchi et al. | 204/418 |
| 4,927,516 | 5/1990 | Yamaguchi et al. | 204/403 |
| 4,968,400 | 11/1990 | Shimomura et al. | 204/403 |

FOREIGN PATENT DOCUMENTS 0235016 9/1987 European Pat. Off.
57-46154 3/1982 Japan.
58-200157 11/1983 Japan.
59-142451 8/1984 Japan.

OTHER PUBLICATIONS

Faulkner, "Chemical Microstructures on Electrodes", Chem. Eng. News, 1984, 27, pp. 28–45.
Oyama et al., "A New Type of Ion-Selective Microelectrodes Using Electropolymerized Thin Films", j-4, Bioelectroanalytical Chemistry Symposium, Honolulu, Hawaii, Oct. 18–23, 1987.
Ohnuki et al., "Permaselectivity of Films Prepared by electrochemical Oxidation of Phenol and Amino-Aromatic Compounds", J. Electroanal. Chem., 158:55–67, 1983.
Heinemann et al., "Polymer Film Chemically Modified Electrode as a Potentiometric Sensor", Anal. Chem. 52:345–346, 1980.

*Primary Examiner*—John Niebling
*Assistant Examiner*—Bruce F. Bell
*Attorney, Agent, or Firm*—Burns, Doane, Swecker & Mathis

[57] ABSTRACT

A film-coated sensor is formed by providing an electrically conductive substrate (2), which has a sectional area of less than $10^{-5}$ cm$^2$, connected to a lead wire (5) at one end of an insulative capillary (1) and inscribed in the capillary (1), and providing a coating film (7) at another end, which is open, of the capillary (1) by an electrolytic polymerization process.

The film-coated sensor obtained has a surface which is uniform, the film coating is easy to control, and since the sensor is not readily susceptible to flow of a specimen fluid, there is little drift and response is quick. Owing to its small size, the sensor is capable of measuring very small samples and of performing measurement upon being directly inserted into a living body or tissue.

The sensor can be used also as an enzyme sensor by coating the surface of the film-coated sensor with a fixing enzyme film.

3 Claims, 13 Drawing Sheets

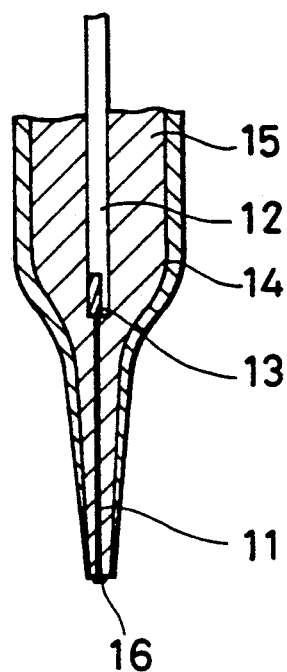
F I g . 6

FILM-COATED SENSOR

TECHNICAL FIELD

This invention relates to a film-coated sensor and, more particularly, to a solid-film-type, miniature film-coated sensor capable of being used upon being inserted into a living body.

BACKGROUND ART

A solid-film-type film-coated sensor has long been desired in the fields of medicine and foods. Film-coated sensors of the coated wire electrode-type, in which a platinum electrode is directly coated with a polymeric film (e.g., a cellulose film), have recently appeared on the market. However, these sensors exhibit problems in terms of durability.

For example, in a solid-film-type oxygen sensor, the rate at which oxygen in a specimen solution is determined by an internal response electrode is limited. Though this problem can be solved if the film thickness of a gas-permeable membrane is reduced and the area of the responsive portion of the sensor is increased, the sensor is readily influenced by flow of the specimen solution, and this is a cause of response drift. Accordingly, in a case where a small amount (on the order of 1 $\mu l$) of a specimen solution is to be measured, it is preferred that the form of the sensor be such that the area having the oxgyen-reducing function be very small (on the order of square microns). In particular, in a case where a miniature sensor is directly inserted into a living body to continuously measure the partial pressure of oxygen in a solution containing a substance to be reduced, it is preferred that the oxygen sensor be one in which coexisting substances are excluded and only the oxygen is acted upon by the oxygen-reducing reaction efficiently by way of an oxygen-reducing membrane. It is especially desired that the sensor have a very small area also from the standpoint of excluding the coexisting substances.

With an oxygen sensor in which the gas-permeable membrane is further coated with an enzyme-fixing membrane, time is required for the permeation of oxygen gas and response time (a 90% response) takes more than one minute.

Thus, there is increasing demand for a quick-response, miniaturized film-coated sensor in which a solid film coating is readily controlled, and in which there is little drift.

Furthermore, when measurement is performed in a blood component, accurate measurement is made impossible owing to adhesion of protein to the surface of a platinum electrode.

DISCLOSURE OF THE INVENTION

An object of the present invention is to solve the foregoing problems of the prior art and provide a miniature film-coated sensor in which the surface is uniform, the film coating is readily controlled and there is little drift because the sensor is not readily influenced by the flow of the specimen solution.

A further object of the invention is to provide a film-coated sensor which has a quick response and which is not readily influenced by electrode-activated substances other than substances to be measured that are present in solution. In particular, an object of the invention is to provide a film-coated sensor having a quick response of less than 10 seconds.

Thus, there is provided a film-coated sensor capable of measuring trace amounts (less than 10 $\mu l$) of a sample and of performing measurement upon being directly inserted into a living body or tissue.

In order to attain the foregoing objects, a film-coated sensor according to the present invention comprises a capillary, an electrically conductive substrate connected to a lead wire at one end of the capillary and inscribed in the capillary, and a solid coating film which coats, to a predetermined depth, an end face of the electrically conductive substrate at another end, which is open, of the capillary.

The electrically conductive substrate is composed of carbon fibers, a carbon rod-shaped member, gold wire or a metal oxide.

The sectional area of the electrically conductive substrate is less than $10^{-5}$ cm$^2$.

The solid coating film has a film which responds only to a gas or electrolyte from an activated substance of interest contained in blood or a related biological fluid.

According to the present invention, there can be provided a miniature film-coated sensor in which the surface is uniform, the film coating is readily controlled and there is little drift because the sensor is not readily influenced by the flow of the specimen solution.

Further, there can be provided a film-coated sensor which has a quick response and which is not readily influenced by electrode-activated substances other than substances to be measured that are present in solution. In particular, there can be provided a film-coated sensor having a quick response of less than 10 seconds.

Thus, there is provided a film-coated sensor capable of measuring trace amounts (less than 10 $\mu l$) of a sample and of performing measurement upon being directly inserted into a living body or tissue. Furthermore the film-coated sensor of the present invention is capable of being mass-produced since the sensor characteristics are uniform.

More particularly, in a case where the present invention is applied to an oxygen sensor, the following advantages are obtained:

(i) As for the electrochemical behavior (the redox reaction response) of $Fe(CN)_6^{3-}$, $Fe(CN)_6^{4-}$ of a carbon electrode, the redox wire is symmetrical and the current value is substantially constant, irrespective of electrode surface area, when the sectional area of the responsive portion of the electrode is less than $10^{-5}$ cm$^2$, preferably $2.83 \times 10^{-7}$ cm$^2$.

(ii) Drift is almost non-existent as a result of using a film-coated oxygen electrode in which a carbon electrode base is directly coated with an oxygen gas-responsive reducing film.

(iii) Though the residual current value calculated from oxygen partial pressure vs. current density increases as the area of the electrode base decreases, the residual current is constant, on the order of $1 \times 10^{-4}$ (A/cm$^2$), for a sectional area of less than $10^{-5}$ cm$^2$.

(iv) As for the electrolytic conditions of the film coating when the carbon electrode is coated with the oxygen gas-responsive reducing film, control of electrolytic reaction time is limited to a very short time of less than 10 seconds, by way of example, if the sectional area of the responsive portion of the electrode is greater than $10^{-5}$ cm$^2$. However, if this sectional area is less than $10^{-5}$ cm$^2$, control of the electrolytic film coating is possible over an extended time period of more than 60 seconds (more than one minute).

If the invention is applied to an enzyme sensor, on the other hand, the electrode area will be ultraminiaturized. The following advantages are obtained as a result:

(1) Basic concentration measurement in a living body or tissue is possible.

(2) Measurement of trace amounts of a sample on the μl order is of course possible.

(3) Since the sensor substrate is ultraminiaturized, response is a very quick three seconds and rapid measurement is possible.

(4) Cost is low since inexpensive carbon fiber can be used.

(5) A change in concentration caused by reaction is negligible owing to the very small responsive area.

(6) The influence of solution fluidity and flow is negligible.

Other objects and effects will become apparent from a description of embodiments with reference to the following drawings.

BRIEF DESCRIPTION OF THE DRAWINGS

FIG. 6 is a schematic view showing the structure of an oxygen sensor fabricated according to Embodiment 2;

BEST MODE FOR CARRYING OUT THE INVENTION

Embodiments of the present invention will now be described while referring to the accompanying drawings. In these embodiments, a film-coated sensor is typified by an oxygen sensor and an enzyme sensor employing the oxygen sensor. However, the present invention is applied similarly to other film-coated sensors as well.

The oxygen sensors of these embodiments are miniature oxygen sensors in which the rod-shaped cross section of a carbon material including carbon fiber material is made less than $10^{-5}$ cm$^2$ and is directly coated with an oxygen gas-responsive reducing film. According to these embodiments, the sectional area of the responsive portion is less than $1 \times 10^{-5}$ cm$^2$ (which corresponds to 3-4 carbon fibers, where the diameter of one carbon fiber is 6 m), preferably $2.83 \times 10^{-7}$ cm$_2$ (which corresponds to one carbon fiber).

Electrically conductive carbon is ideal as an electrically conductive substrate. Examples which can be mentioned are basal plane pyrolytic graphite, glassy carbon and the like. Among these, electrically conductive carbon having a graphite crystal structure is especially preferred.

Embodiment 1

(Process for manufacturing carbon-graphite electrode)

Figure 1A:
FIG. 1A is a diagram illustrating a glass capillary of Embodiment 1.

Two capillaries 1 of a shape comprising a main-body portion 1b and a capillary tube portion 1a shown in FIG. 1A were fabricated by extending glass tubes having an outer diameter of 3 mm and a length of 5 cm using a miniature electrode manufacturing apparatus. A carbon fiber 2 (Besfighte, manufactured by Toho Rayon) was inserted into the capillary tube portion 1a (the extended portion) of one of the capillaries 1, and the gap between the capillary tube and the carbon fiber was filled with electron wax 3 (manufactured by So Denshi Kogyo) serving as an insulative bonding agent, thereby insulating the carbon fiber. Silver paste 4 serving as an electrically conductive bonding agent was injected from the other end, a lead wire 5 was inserted from this end to achieve an electrical connection, and this end was sealed and the lead wire 5 fixed by an insulative bonding agent 6 in such a manner as to prevent leakage of the silver paste 4. Further, the tip of the capillary tube portion was polished (0.5 μm sandpaper, PR1-24, manufactured by 3M Company). A carbon-fiber electrode 10 was thus completed.

Figure 1B:
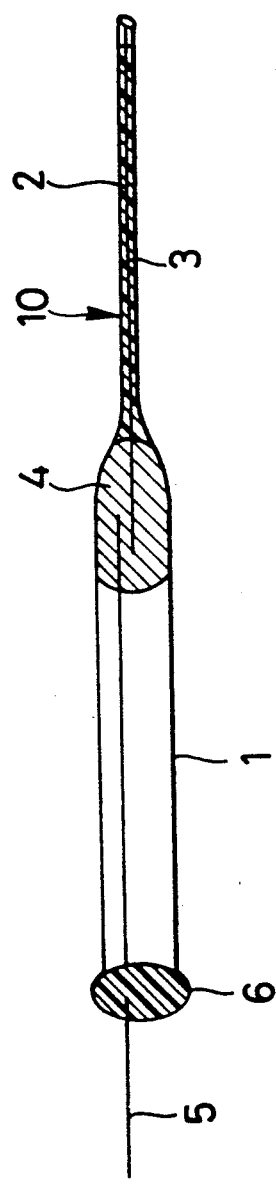
FIG. 1B is a diagram illustrating the structure of a carbon-fiber electrode of Embodiment 1.

A schematic view of the carbon-fiber electrode 10 is shown in FIG. 1B. Here a glass tube is used as the capillary 1, although the invention is not limited to a glass tube so long as an insulative capillary tube is obtained by heating or drawing. Materials which can be used are polyvinyl chloride, polypropylene, polystyrene, etc.

(Manufacture of miniature oxygen sensor)

By employing a method illustrated below, the surface of the carbon fiber 2 of the above-described carbon-fiber electrode 10 was coated with an electrolytic polymeric film 7 made of meso-tetra (o-aminophenyl) cobalt porphyrin (abbreviated to Co-TAPP).

By using a three-electrode cell having the carbon-fiber electrode 10 as an active electrode, an Ag/AgCl electrode available on the market as a reference electrode and a platinum coil as an opposing electrode, the electrolytic polymeric film 7 was deposited by performing electrolysis for 60 seconds at a constant potential of +1.8 volts (vs. Ag/AgCl) in an electrolyte having the following composition:

TABLE 1

| CARBON FIBER | | CURRENT DENSITY (A/cm$^2$) | | | | RESIDUAL CURRENT (A/cm$^2$) |
| --- | --- | --- | --- | --- | --- | --- |
| NUMBER OF FIBERS | AREA (cm$^2$) | PO$_2$ (mmHg) | | | | |
| | | 20 mmHG | 60 mmHg | 85 mmHg | 128 mmHg | |
| 1 | $2.826 \times 10^{-7}$ | $1.305 \times 10^{-4}$ | $1.491 \times 10^{-3}$ | $2.269 \times 10^{-3}$ | $2.994 \times 10^{-3}$ | $1.484 \times 10^{-4}$ |
| 10 | $2.826 \times 10^{-6}$ | $1.789 \times 10^{-3}$ | $5.315 \times 10^{-3}$ | $8.185 \times 10^{-3}$ | $1.189 \times 10^{-3}$ | $1.542 \times 10^{-4}$ |
| 30 | $8.478 \times 10^{-6}$ | $1.011 \times 10^{-3}$ | $2.998 \times 10^{-3}$ | $4.329 \times 10^{-3}$ | $6.395 \times 10^{-3}$ | $1.770 \times 10^{-4}$ |
| 100 | $2.826 \times 10^{-5}$ | $5.987 \times 10^{-4}$ | $2.265 \times 10^{-3}$ | $3.154 \times 10^{-3}$ | $4.604 \times 10^{-3}$ | $0.652 \times 10^{-4}$ |

| Electrolyte Composition | 1 mM | Co-TAPP |
| --- | --- | --- |
| | 0.1 M | NaClO$_4$ |
| | Solvent | acetonitrile |

Figure 2:
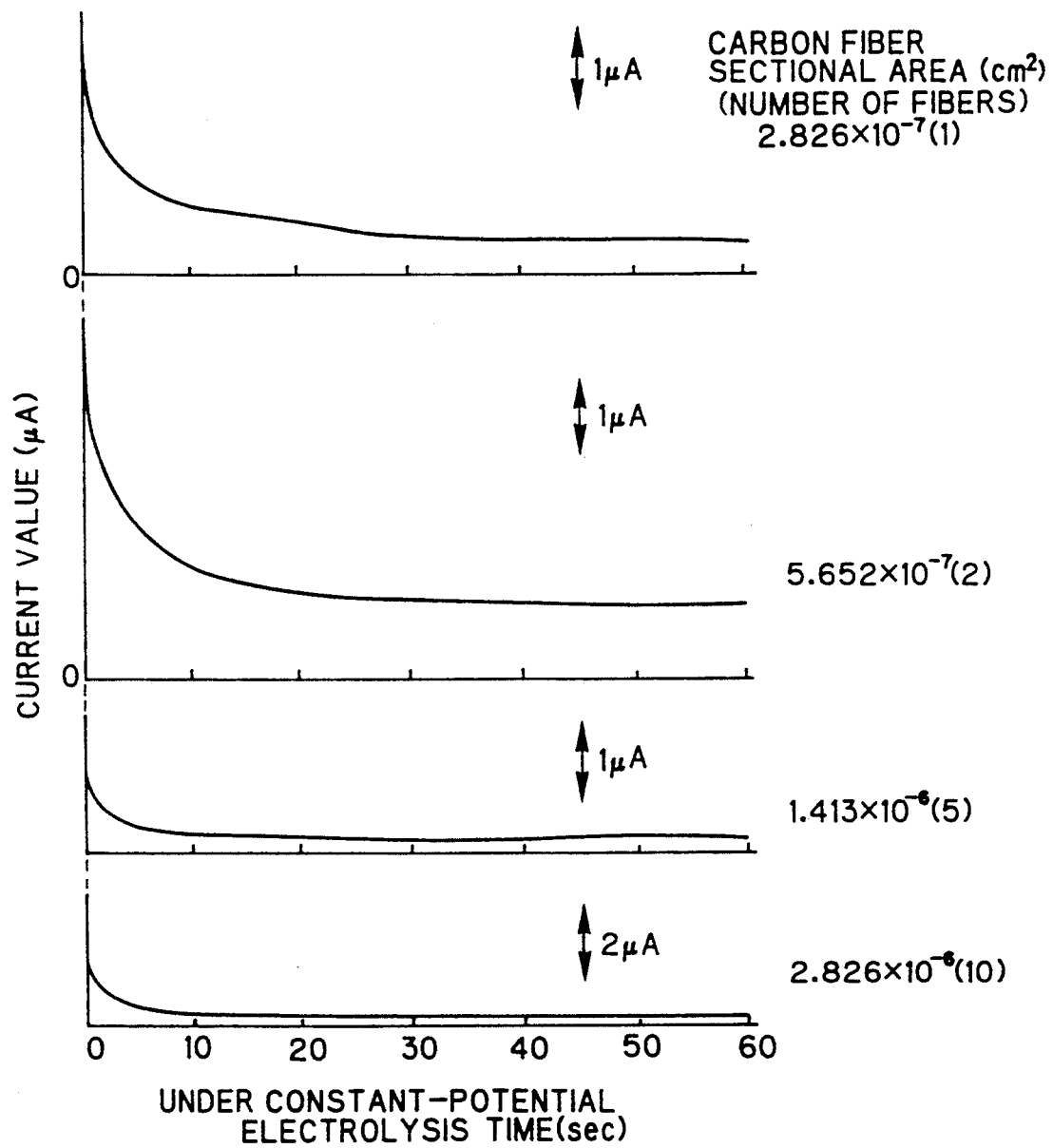
FIG. 2 is a diagram illustrating a current change in constant-current electrolysis during preparation of an electrolytic polymeric film.

The current change of constant-potential electrolysis at this time is shown in FIG. 2. The time for convergence to a constant current is about 60 seconds. For purposes of comparison, the current value becomes constant in 40 seconds in case of two carbon fibers (sectional area: $5.652 \times 10^{-7}$ cm$^2$) and in 20 seconds in case of five carbon fibers (sectional area: $1.413 \times 10^{-6}$ cm$^2$). A thin film is formed in this sequence and film deposition control is shortened.

Figure 1C:
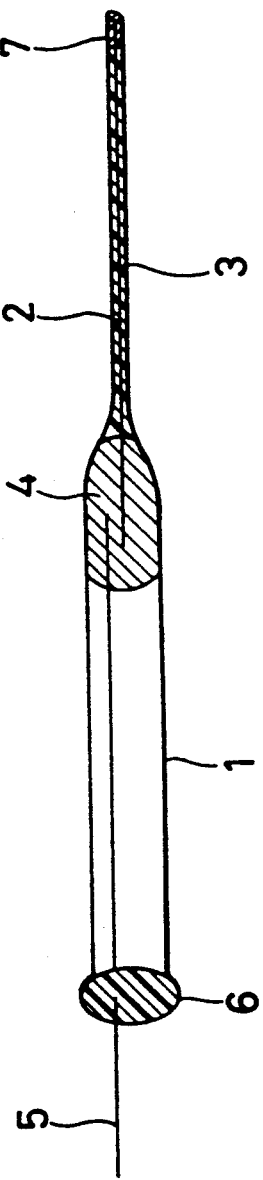
FIG. 1C is a diagram illustrating the structure of an oxygen sensor of Embodiment 1.

A schematic view of the oxygen sensor thus manufactured is illustrated in FIG. 1C.

Experiment 1

By employing an electrode cell using the miniature carbon-fiber electrode shown in FIG. 1B of Embodiment 1 as an active electrode, a saturated sodium chloride calomel electrode as a reference electrode and a platinum mesh as an opposing electrode, measurement of the cyclic voltammetry of a redox reaction of Fe(CN)$_6^{3-}$ and Fe(CN)$_6^{4-}$ on the surface of a miniature oxygen electrode was measured in the following electrolyte:

20 mM Fe(CN)$_6^{3-}$
0.1 M NaClO$_4$

Figure 3A:
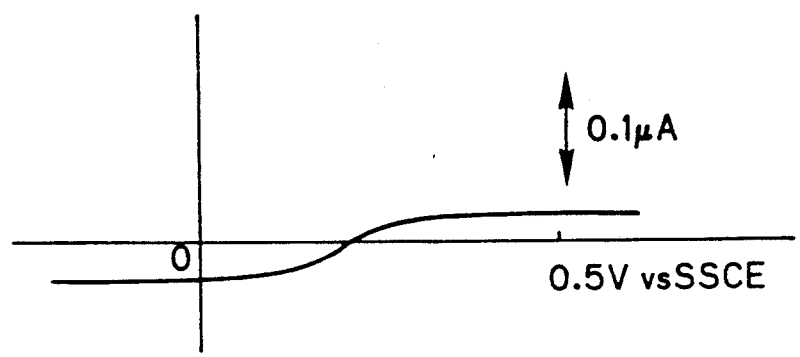
FIGS. 3A through 3C are diagrams showing cyclic voltammograms of redox reactions of a miniature carbon-fiber electrode of Embodiment 1.
Figure 3B:
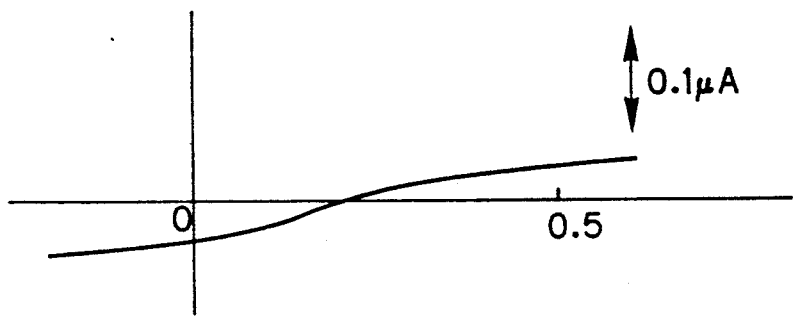
Figure 3C:
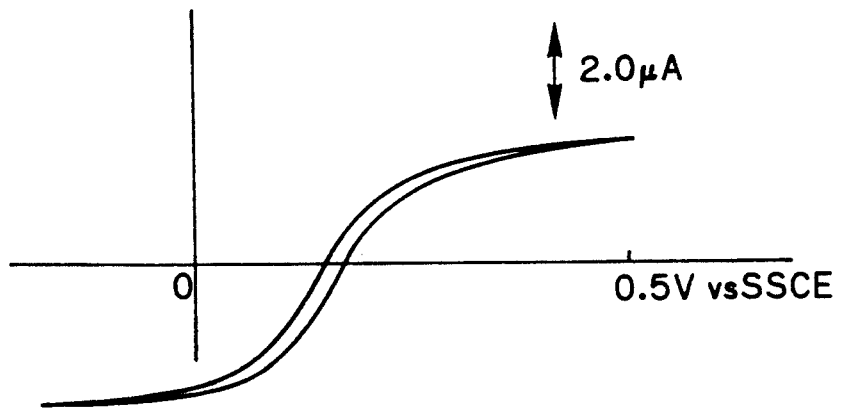

The results are shown in FIG. 3(a). Cyclic voltammograms for carbon-fiber sectional areas of $1.413 \times 10^{-6}$ cm$^2$ (a five-fiber bundle) and $2.826 \times 10^{-5}$ cm$^2$ (a 100-fiber bundle) are shown in FIGS. 3B and 3C for purposes of comparison.

As a result, it was confirmed that while the redox current value becomes approximately constant in FIG. 3A, the redox current value varies with a change in potential value when the sectional area of the carbon fibers is $1.413 \times 10^{-6}$ cm$^2$ (a bundle of five or more carbon fibers).

Accordingly, when it is attempted to obtain a constant current value, the sectional area of the carbon electrode should be less than about $10^{-5}$ cm$^2$, and an ideal sectional area is $2.83 \times 10^{-7}$ cm$^2$ (which corresponds to one carbon fiber).

Experiment 2

Figure 4:
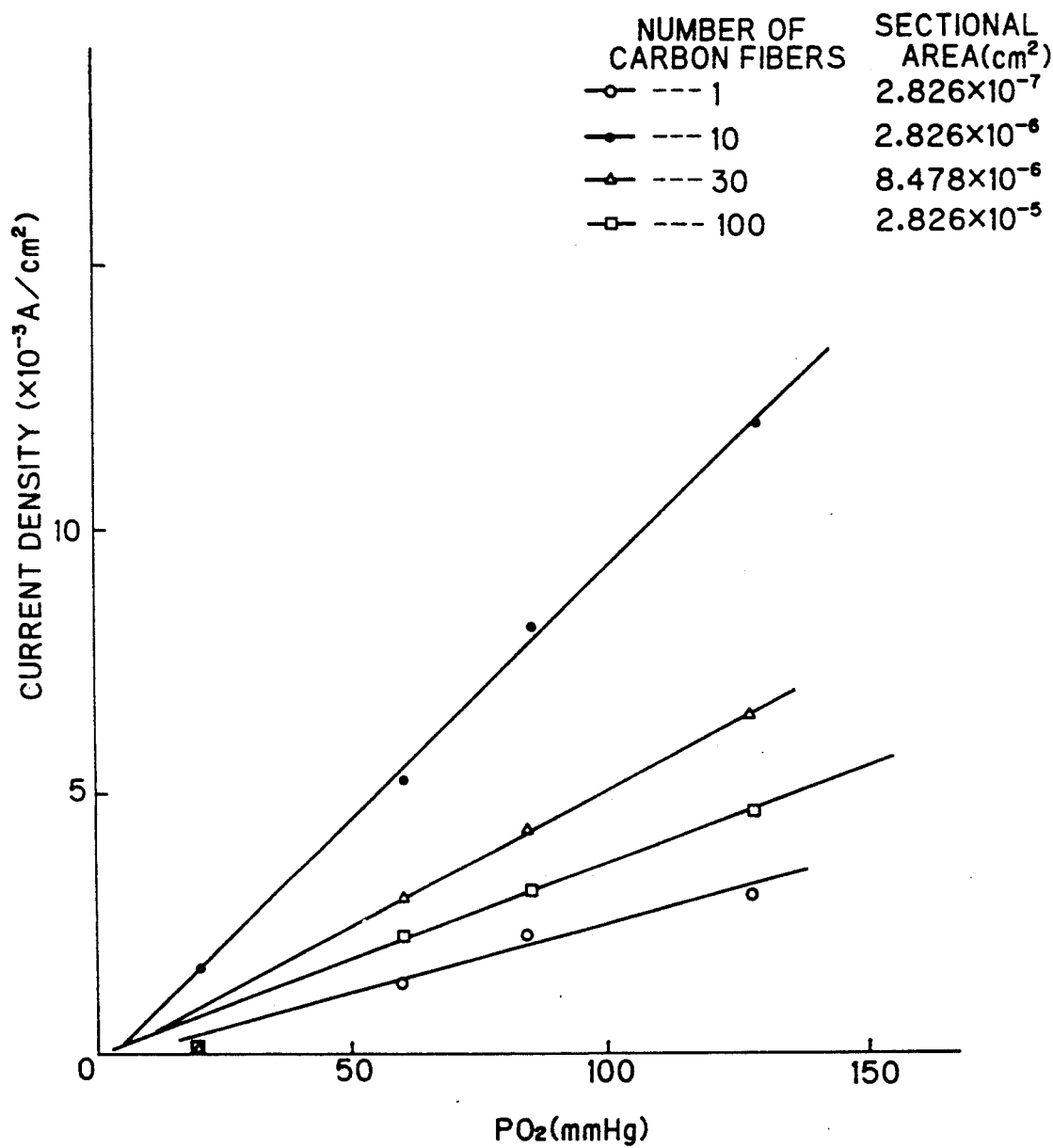
FIG. 4 is a diagram in which the relationship between current density and partial pressure of oxygen of an oxygen sensor according to Embodiment 1 is plotted in a case where the area of the responsive portion of the electrode is varied.

The relationship between current density (A/cm$^2$) and partial pressure of oxygen (mmHg) when the area of the responsive portion of the electrode is varied from $2.826 \times 10^{-7}$ cm$^2$ to $2.826 \times 10^{-5}$ cm$^2$ is illustrated in Table 1 and in FIG. 4, in which this relationship is plotted. The oxygen sensor used was that fabricated in Experiment 1. Measurement was performed at different partial pressures of oxygen of 20, 60, 85 and 128 mmHg using N$_2$ gas as an inert gas. When residual current is obtained from the relationship between current density and the pO$_2$ partial pressure, the result is the residual-current column of Table 1.

As a result, when the area of the responsive portion of the electrode is less than $8.478 \times 10^{-6}$ cm$^2$ (a bundle of five fibers), residual current converges to a value between $1.484 \times 10^{-4}$ A/cm$^2$ and $1.770 \times 10^{-4}$ A/cm$^2$.

Experiment 3

Figure 5A:
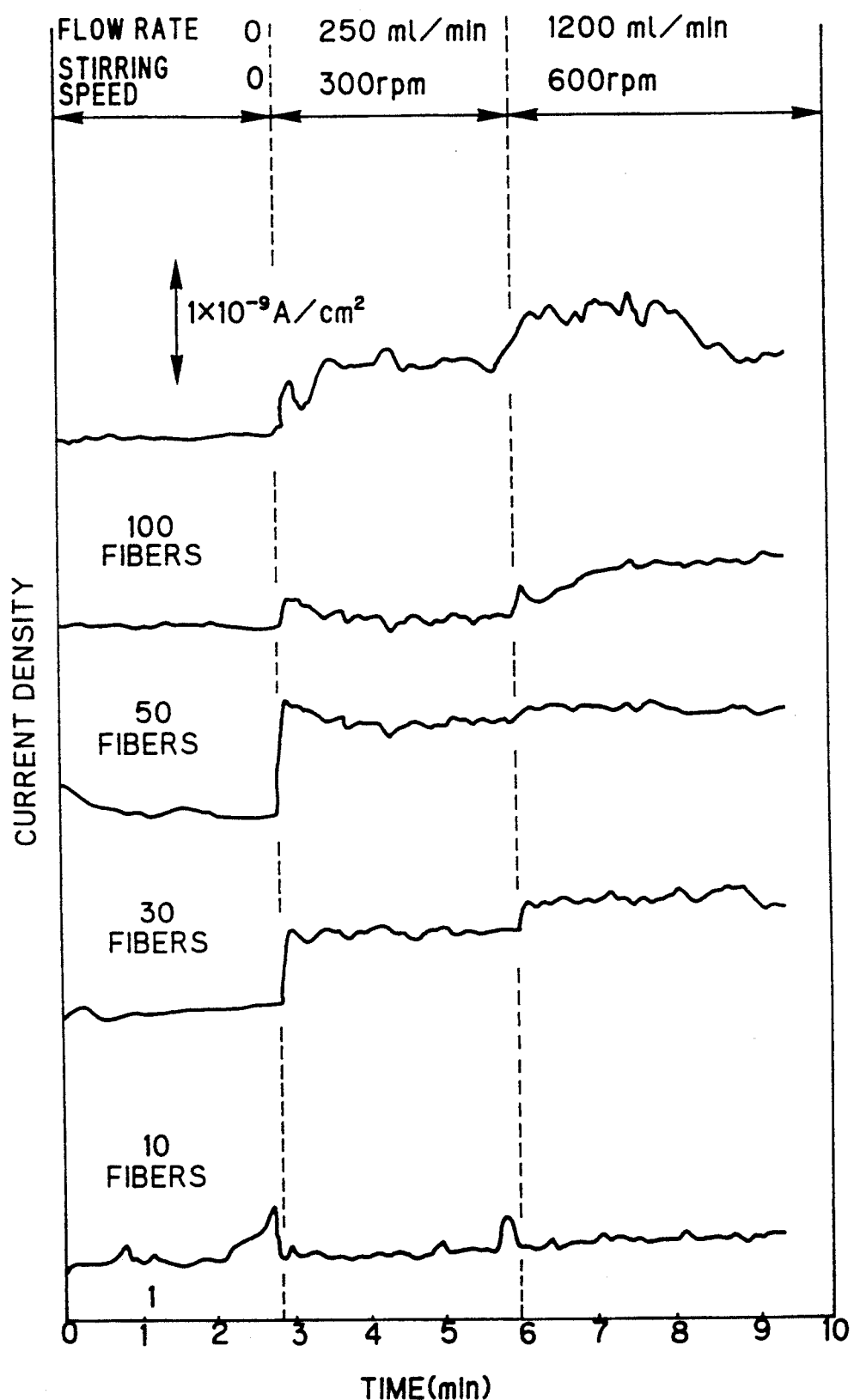
FIG. 5A is a diagram showing electrode drift due to the influence of flow in the oxygen sensor of Embodiment 1.

By using the oxygen sensor of the embodiment in the same manner as Experiment 2, electrode drift (a variance in current density) due to the influence of flow of the specimen solution was examined in an electrolyte solution (a phosphate buffer solution having a pH of 7.4) under constant conditions where the oxygen concentration was 140 mmHg and temperature was adjusted to $37 \pm 0.05°$ C. The results are shown in FIG. 5A, where the stirring speed of a stirrer for stirring the specimen solution was varied and flow rate was changed over between 250 ml/min and 1200 ml/min.

The Figure shows that drift tends to increase as electrode area increases in the manner $2.826 \times 10^{-7}$ cm$^2$, $2.826 \times 10^{-6}$ cm$^2$, $8.478 \times 10^{-6}$ cm$^2$ and $2.826 \times 10^{-5}$ cm$^2$. Accordingly, electrode area should be between $2.826 \times 10^{-7}$ cm$^2$ (one carbon fiber) and $2.826 \times 10^{-6}$ cm$^2$ (ten carbon fibers). The value of $2.826 \times 10^{-7}$ cm$^2$ (one carbon fiber) is preferred, as drift becomes small at this value. This is deemed to be best for attaining the present object.

Thus, the oxygen sensor of the present embodiment has the following advantages:

(i) as for the electrochemical behavior (the redox reaction response) of Fe(CN)$_6^{3-}$, Fe(CN)$_6^{4-}$ of a carbon electrode, the redox wave is symmetrical and the current value is substantially constant, irrespective of electrode surface area, when the sectional area of the responsive portion of the electrode is less than $10^{-5}$ cm$^2$, preferably $2.83 \times 10^{-7}$ cm$^2$.

(ii) Drift is almost non-existent as a result of using a film-coated oxygen electrode in which a carbon electrode base is directly coated with an oxygen gas-responsive reducing film.

(iii) Though the residual current value calculated from oxygen partial pressure vs. current density increases as the sectional area of the carbon electrode decreases, the residual current is constant, on the order of $1 \times 10^{-4}$ (A/cm$^2$), for a sectional area of less than $10^{-5}$ cm$^2$.

(iv) As for the electrolytic conditions of the film coating when the carbon electrode is coated with the oxygen gas-responsive reducing film, control of electrolytic reaction time is limited to a very short time of less than 10 seconds, by way of example, if the sectional area of the responsive portion of the electrode is greater than $10^{-5}$ cm$^2$. However, if this sectional area is less than $10^{-5}$ cm$^2$, control of the electrolytic film coating is possible over an extended time period of more than 60 seconds (more than one minute).

Experiment 4

By using the oxygen sensor fabricated in Experiment 1, the surface concentration of the electrolytic polymeric film (the Co-TAPP film) was measured with respect to electrode area when the area of the responsive portion of the electrode was made $7.85 \times 10^{-7}$ cm$^2$, $7.85 \times 10^{-6}$ cm$^2$ and $7.85 \times 10.5$ cm$^2$.

Figure 5B:
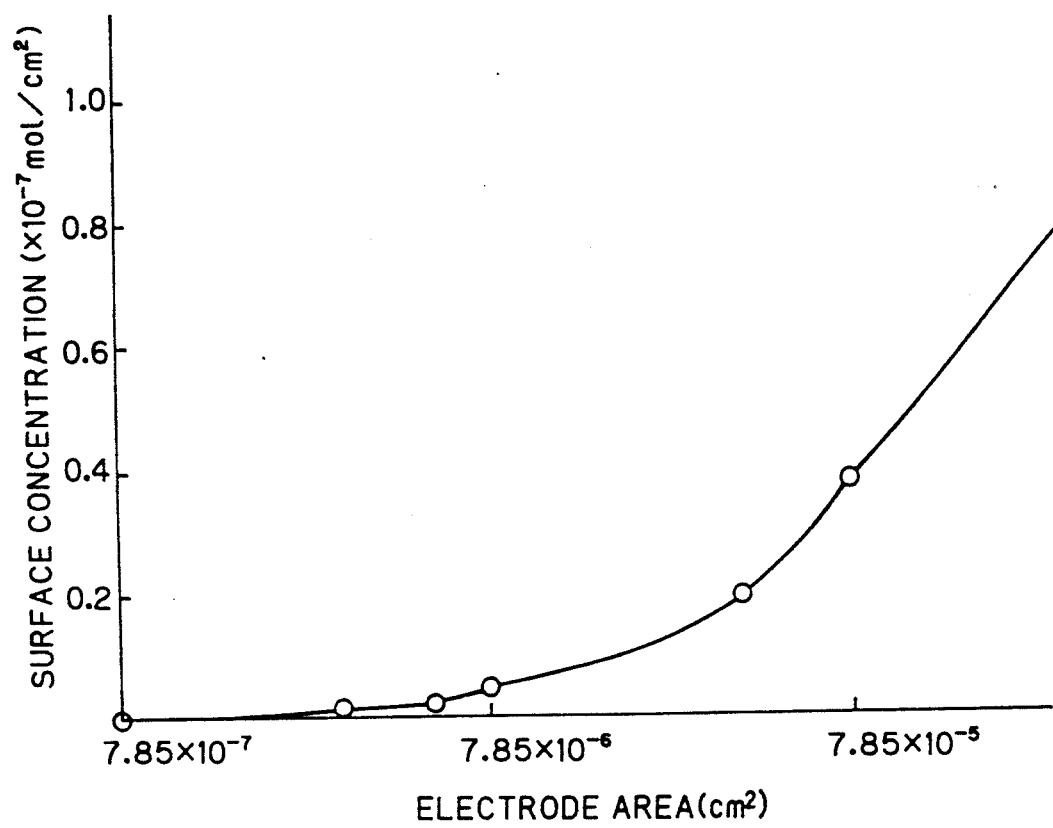
FIG. 5B is a diagram showing the surface concentration and electrode area of the oxygen sensor of Embodiment 1.

As shown in FIG. 5b, the surface concentration of the Co-TAPP increases as electrode area increases at areas greater than $7.85 \times 10^{-6}$ cm$^2$. However, there is almost no change at areas less than $7.85 \times 10^{-6}$ cm$^2$. This facilitates uniformalization of sensor characteristics and make possible mass production of the film-coated sensor.

Measurement was performed at an oxygen concentration of 0 mmHg (bubbling in N$_2$) in an electrolytic solution (a phosphate buffer solution having a pH of 7.4) at room temperature.

Experiment 5

By using the oxygen sensor fabricated in Experiment 1, potential sweep speed $\{v^{\frac{1}{2}}=(\text{mV/sec})^{\frac{1}{2}}\}$ of a voltammogram) obtained when the area of the responsive portion of the electrode is made $7.85 \times 10^{-7}$ cm$^2$, $3.14 \times 10^{-6}$ cm$^2$ and $7.85 \times 10^{-6}$ cm$^2$ was investigated.

Figure 5C:
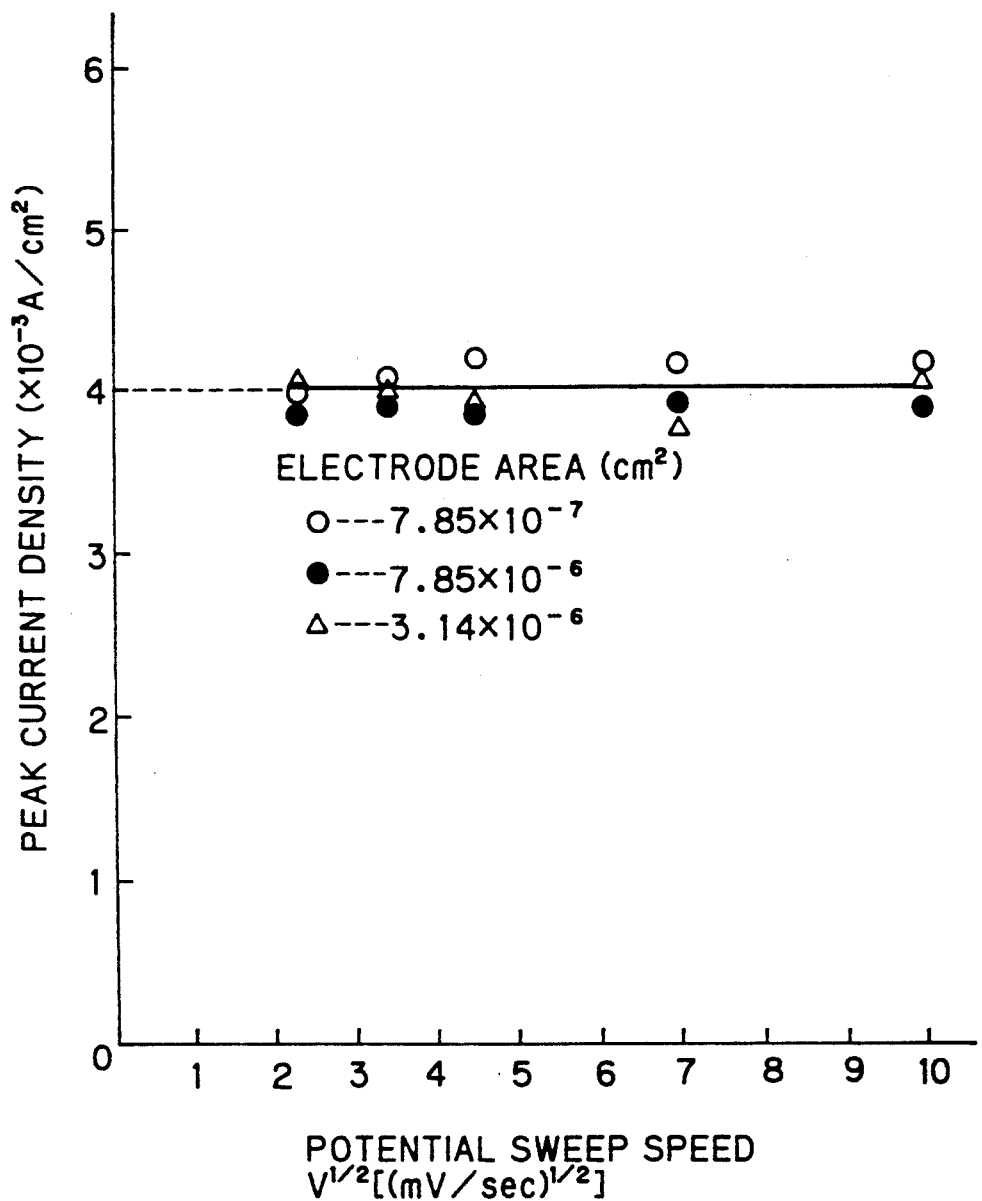
FIG. 5C is a diagram showing the relationship between peak current density and potential sweep velocity of the oxygen sensor of Embodiment 1.

As evident from FIG. 5C, peak current becomes constant over a wide range, and it will be understood that the sensor has satisfactory characteristics for use as a miniature electrode.

Measurement was performed in an electrolyte solution (a phosphate buffer solution having a pH of 7.4) saturated with oxygen (500 mmHg) at room temperature.

In the present embodiment, the sensor is fabricated by integrating the main portion 1b and the capillary portion 1a. However, the sensor can be fabricated by coating and insulating the carbon fiber, with the exception of both ends thereof, with an insulator such as polyethylene fluoride tube or enamel, coating one end with the electrolytic polymeric film 7, connecting the other end to the lead wire via the electrically conductive bonding agent 6, thereby forming the main-body portion 1b and the capillary portion 1a separately, and then uniting these two portions.

The film-coated sensor of the embodiment described next is an ultraminiature oxygen sensor in which one filament of a carbon fiber is adopted as an electrically conductive substrate the surface whereof is coated with a cobalt-porphyrin polymeric film, which possesses an oxygen-reducing catalytic function, using an electrolytic polymerization process. It is possible to make the outer diameter of the sensor tip 10 to 50 μm to measure a very small sample on the microliter order or to measure oxygen concentration in cells or the nervous system, etc. Since a carbon fiber of less than 10 μm is used as the electrically conductive substrate, speed of response is very high and it is possible to measure oxygen concentration within one second at 90% response. In addition, there is almost no influence from pulsation.

Embodiment 2

The structure of an oxygen sensor fabricated according to this embodiment is shown schematically in FIG. 6. The procedure for fabrication will now be described.

(1) A conductor 12 is connected to one end of a carbon fiber 11 (10 μmφ, manufactured by Union Carbide) by means of an electrically conductive bonding agent 13. The fiber is inserted into a glass capillary 14 and the periphery thereof is insulated by an epoxy bonding agent 15, thereby completing an electrode.

(2) By using a three-electrode cell having this electrode as an active electrode, an Ag/AgCl electrode available on the market as a reference electrode and a platinum coil as an opposing electrode, electrolytic polymerization of mesotetra (o-aminophenyl) cobalt porphyrin (Co-TAPP) is performed in an electrolyte having the following composition:

| Electrolyte Composition | 1 mmol/l | Co-TAPP |
|---|---|---|
| | 0.1 mol/l | NaClO$_4$ |
| | Solvent | acetonitrile |

After sweeping potential from 0 to +1.8 V (vs. SSCE) at 50 mV/sec in the electrolyte, constant-potential electrolysis is carried out at +1.8 V to complete deposition of a Co-TAPP film 16.

The film thickness of the Co-TAPP film 16 in this case was 0.5 μm. A film thickness of 400 Å–50 μm is preferred, particularly a film thickness of 1–10 μm. Sensor characteristics are unsatisfactory below 400 Å, and peeling of the film easily occurs above 50 μm.

Experiment 6

Figure 7A:
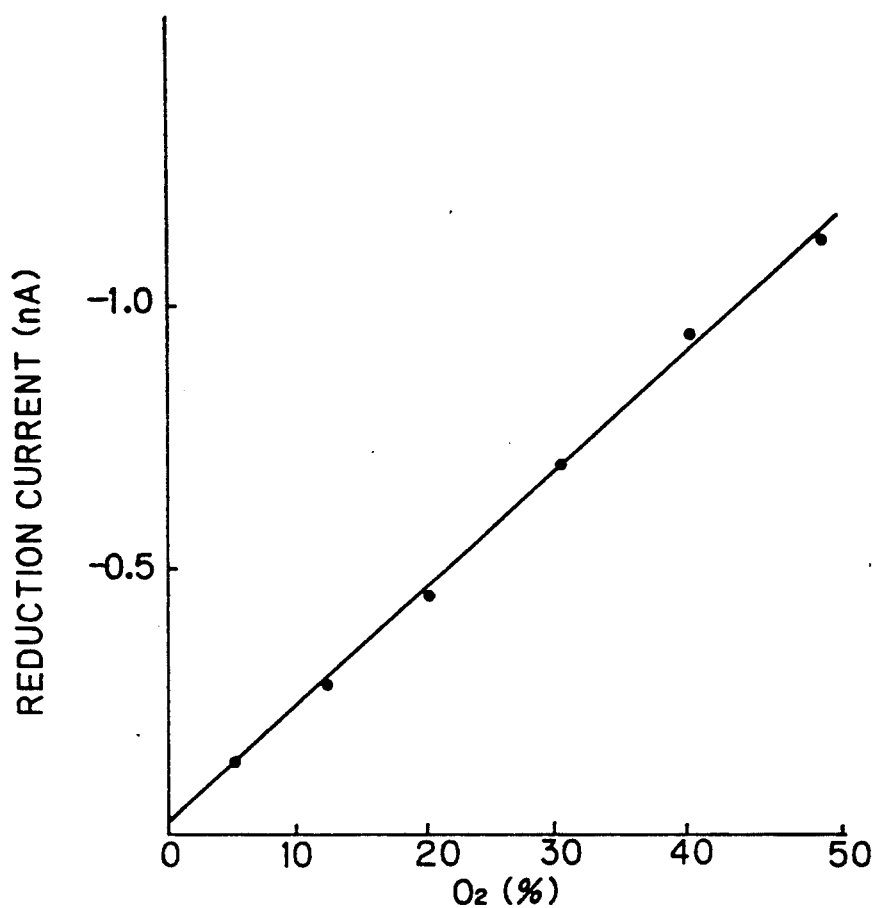
FIGS. 7A and 7B are diagrams showing the response of the oxygen sensor fabricated according to Embodiment 2.
Figure 7B:
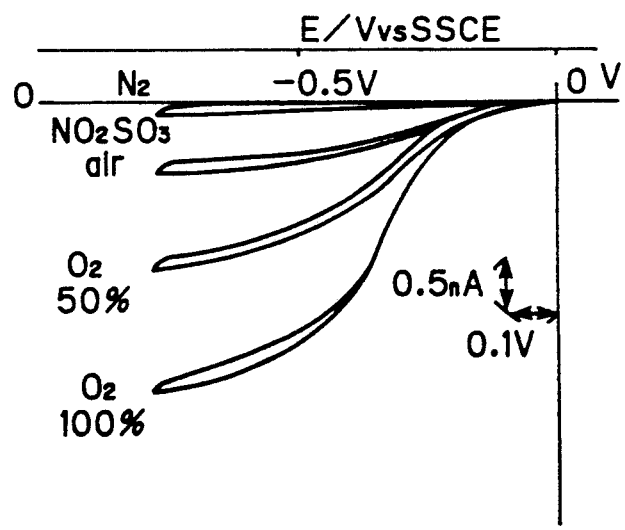

The oxygen sensor fabricated in Embodiment 2 and an Ag/AgCl electrode available on the market were immersed in a 50 mmol/l phosphate buffer solution (pH:7.4), a potential of −0.6 V with respect to the Ag/AgCl electrode was applied to the sensor, and the value of current flow was measured while changing the O$_2$ concentration of the gas passes through the solution. The results are plotted in FIG. 7A. A voltage of −0.6 V was decided from the result of measurement current vs. voltage shown in FIG. 7B.

Excellent linearity over a wide range is established between oxygen concentration (pO$_2$) and current value, and it was found that the sensor acts as an oxygen sensor.

Experiment 7

Figure 8:
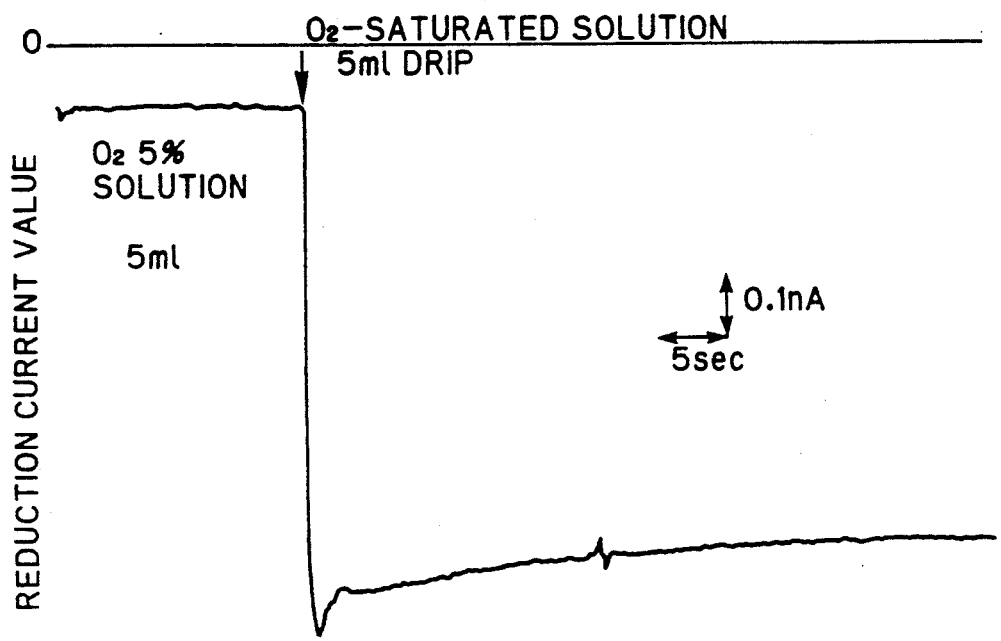
FIG. 8 is a diagram showing the response rate of the oxygen sensor fabricated according to Embodiment 2.

Measurement was performed in a solution having a constant oxygen concentration by a method similar to that of Experiment 6, a solution saturated with oxygen gas was added to this solution, and a change in the current value was investigated. The resulting graph is shown in FIG. 8. It was found that the sensor responded quickly when the solution was added, and that the speed of response was a very quick one to two seconds.

Comparative Example 1

By using a carbon electrode having a diameter of 0.1 mm, an oxygen sensor having a large area was fabricated by coating the surface of the electrode with a Co-TAPP film (film thickness: 0.5 μm) using a method similar to that of Embodiment 2.

Experiment 8

Figure 9:
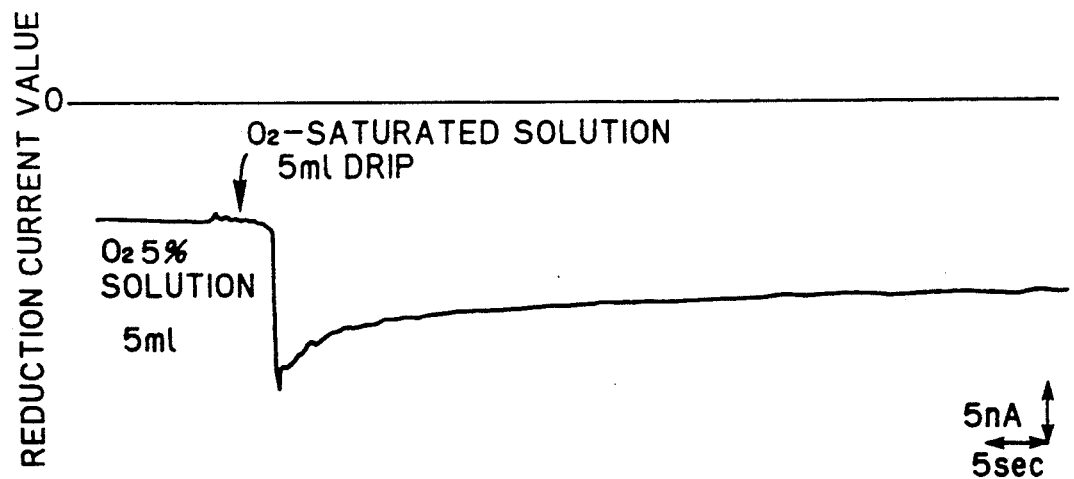
FIG. 9 is a diagram showing the response rate of an oxygen sensor fabricated according to Comparative Example 1.

Measurement similar to that of Experiment 6 was performed in order to compare the sensor of Comparative Example 1 with the sensor fabricated according to Embodiment 2. The results are illustrated in FIG. 9. It was found that current rise is slow and that five to ten seconds were required for response.

Experiment 9

Figure 10A:
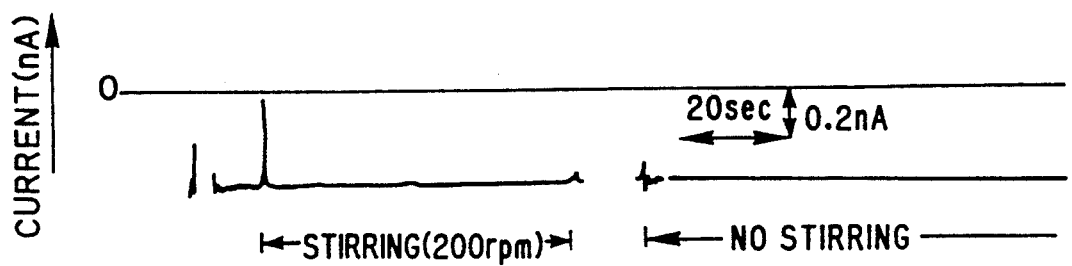
FIGS. 10A and 10B are diagrams showing the influence of flow in the oxygen sensors fabricated according to Embodiment 2 and Comparative Example 1.
Figure 10B:
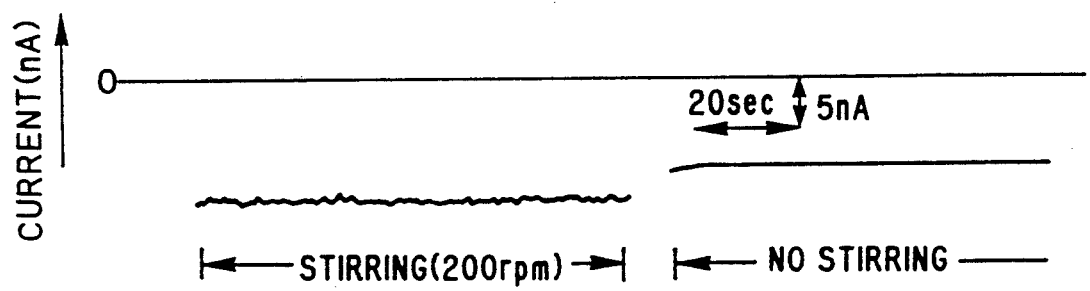

Oxygen sensors created in accordance with Embodiment 2 and Comparative Example 1 were immersed in a phosphate buffer solution along with a reference electrode, current value when a potential of −0.6 V was applied to the reference electrode and the solution was stirred was compared with a case in which the solution was not stirred, and susceptibility to the influence of fluid flow was evaluated. The results are shown in FIGS. 10A and 10B. With the oxygen sensor of Embodiment 2, current value does not change regardless of whether the solution is or is not stirred, as shown in FIG. 10A. With the sensor of Comparative Example 1, however, as shown in FIG. 10B, it was found that while current fluctuates when stirring is performed, fluctuation ceases when stirring is stopped but the current value decreases at such time. On the basis of these results, it was confirmed that the sensor fabricated in accordance with Embodiment 2 is capable of accurate measurement without being influenced by flow of the fluid.

As described in detail above, an oxygen sensor having a quick 90% response of less than one second is obtained by using an electrode having a very small area, namely the cross section of a carbon fiber, and coating this electrode with a film having an oxygen-reducing function. In addition, the oxygen sensor is capable of measuring oxygen concentration without being influenced by other coexisting chemical substances and without being influenced by fluid flow. Furthermore, since the electrode portion is extremely small, measurement is possible with a minute amount of a sample or at a very small region.

In an embodiment described next, an ultraminiature enzyme sensor is provided by achieving miniaturization using one filament of a carbon fiber and forming a thin film on a minute portion using electrolytic polymerization. The purpose is to realize miniaturization and high-speed response and measure substrate concentration in vitro (in tissue) or in a minute amount of a sample. A sensor is provided in which speed of response is less than three seconds for 95% response and the outer diameter of the sensor tip is less than 100 μm (where the responsive portion is less than 10 μm).

Examples of chemical compounds which take part in enzyme reactions and are produced or consumed and exhibit electrode activity are $O_2$, $H_2O_2$, $CO_2$, etc. A cobalt porphyrin polymeric film is preferred as an $O_2$-reducing catalytic film, a poly(4,4'-biphenol) film as an $H_2O_2$-oxidizing catalytic film, and a film comprising polythiophene film/silver/rhenium as a $CO_2$-reducing catalyst. An electrolytic polymerization process is preferred as the coating process for applying these films.

Embodiment 3

Figure 11A:
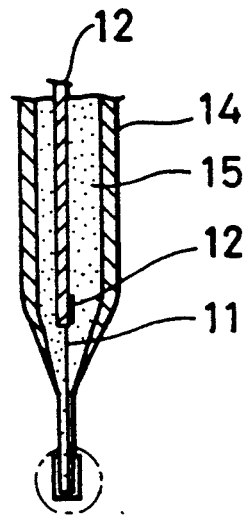
FIG. 11A and FIG. 11B is a schematic view representing the construction of enzyme sensors of Embodiments 4 and 5.
Figure 11B:
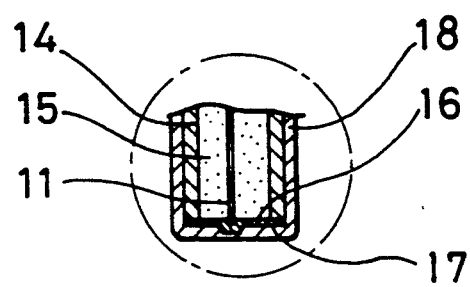

A schematic view showing the construction of an ultraminiature enzyme sensor according to this embodiment is illustrated in FIG. 11. Reference numerals identical with those in FIG. 6 designate the same constituent substances. One end of the carbon fiber 11 is connected to the lead wire 12 using the electrically conductive bonding agent 13, the tip of the carbon fiber is inserted into the finely extended glass capillary 14, and the capillary is subsequently filled with the insulative bonding agent 15 to achieve electrical insulation. Next, a portion of the tip of this capillary electrode is cut off and the cut tip is polished to fabricate a carbon-disk electrode for an ultraminiature enzyme sensor.

By using a potentiostat and a three-electrode system having this ultraminiature disk electrode as an active electrode, a saturated sodium chloride calomel electrode (SSCE) as a reference electrode and a platinum wire as an opposing electrode, electrolysis was performed under the electrolytic conditions indicated below, thereby depositing an electrolytic polymeric film (an oxygen-reducing catalytic film) 16. Using acetonitrile containing 1 mmol/l mesotetra (o-aminophenyl) cobalt porphyrin (hereinafter abbreviated to Co-TAPP) and 0.1 mol/l sodium perchlorate, potential was swept from 0V to 1.8 V (vs. SSCE) at 50 mV/sec, after which constant-potential electrolysis was carried out for 10 minutes at 1.8 V to form a Co-TAPP polymeric film having a film thickness of 0.5 μm.

Experiment 10

Figure 12:
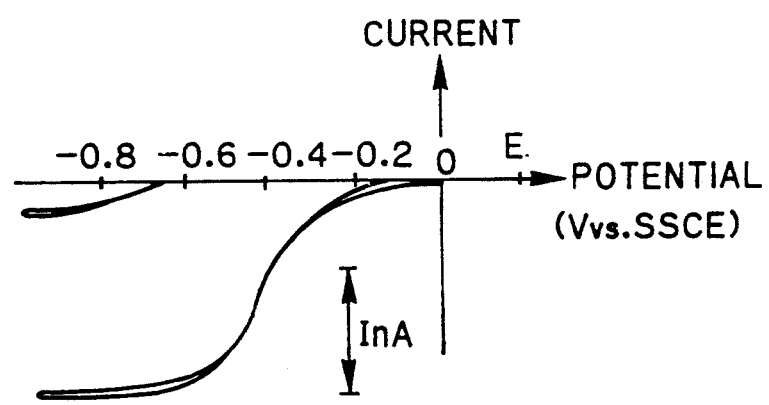
FIG. 12 is a diagram representing cyclic voltammetric response with respect to enzyme reduction of an electrode coated with an enzyme-reducing catalytic film of Embodiment 3.

It will be understood from the cyclic voltammogram shown in FIG. 12 that the electrode thus manufactured catalyzes the electrolytic reducing reaction of oxygen in solution. Specifically, in comparison solely with a carbon-fiber electrode, the oxygen reducing reaction occurs at a potential of −500 to −600 mV, and a steady current is obtained even at a sweep speed of 50 mV/sec.

It was found that by using this electrode, sufficient characteristics as an electrode for a subminiature enzyme sensor were obtained, namely a response time of less than one second when the electrolytic potential was held at −0.6 V (vs. SSCE) and the concentration of oxygen in solution was changed from $PO_2 = 150$ mmHg to 300 mmHg. It will be understood that this oxygen-reducing catalytic-film electrode functions as an oxygen sensor with a very high speed of response.

Embodiment 4

The surface of the electrolytic polymeric film (the oxygen-reducing catalytic film) was coated with an enzyme-fixing film 17 by a method described below.

An oxygen-reducing catalytic-film electrode was immersed five times in a solution obtained by dissolving 100 mg/ml of glucose oxidase and 15 weight.% of bovine serum albumin in a pH 8.0 phosphate buffer solution. After the electrode was allowed to dry, a cross-linking reaction was allowed to take place for 12 hours in a glutaric aldehyde vapor of a 50% glutaric aldehyde solution. This was followed by washing with a 20% glycine solution.

Thus, a glucose oxidase-fixing film was formed (film thickness: 10 μm) to fabricate an ultraminiature enzyme sensor.

Experiment 11

Figure 13:
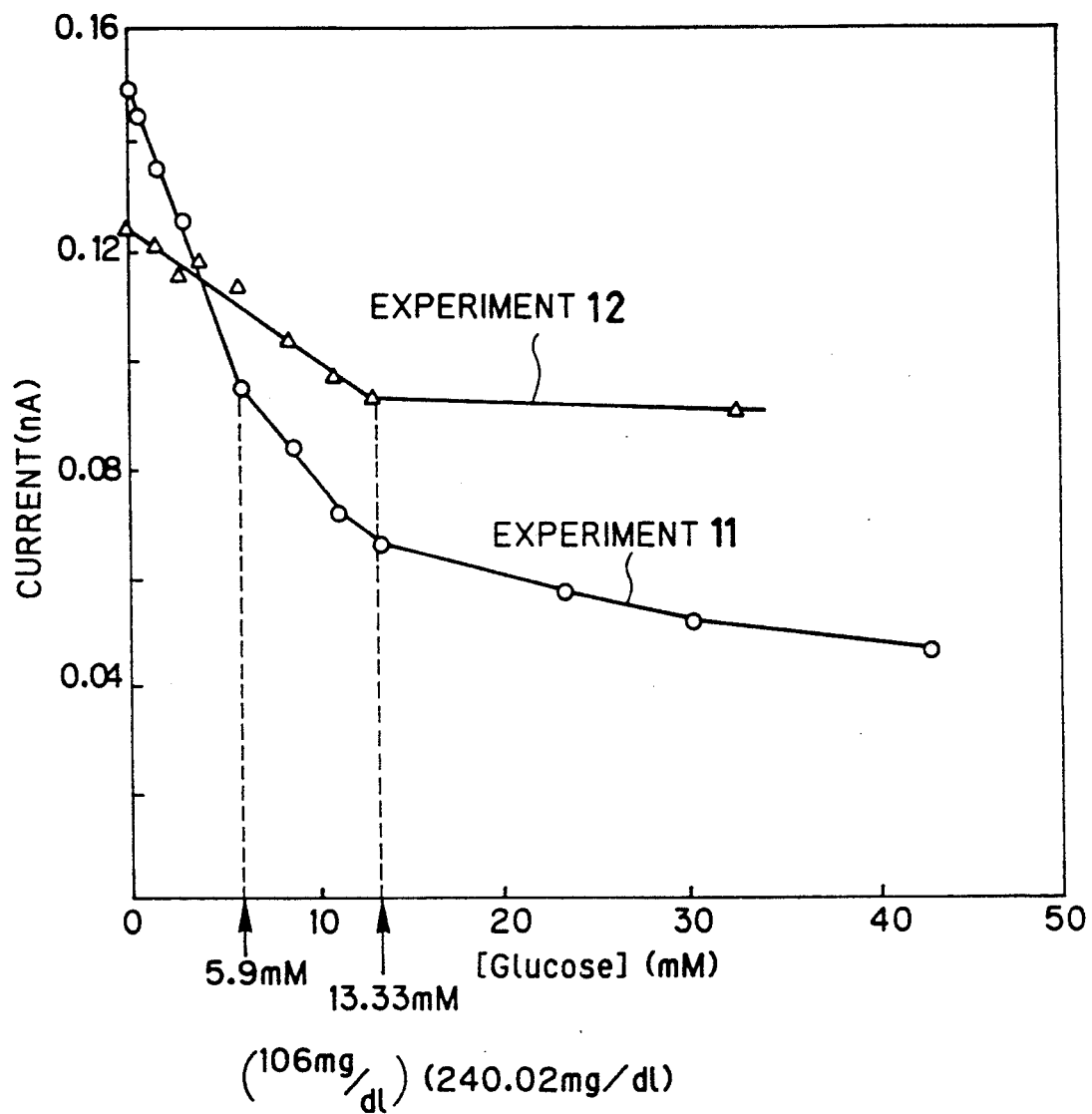
FIG. 13 is a diagram showing current response with respect to a change in glucose concentration of a glucose sensor of Embodiments 4 and 5.

Constant-potential electrolysis at −0.6 V vs. SSCE was performed with a three-electrode cell using the subminiature enzyme sensor of Embodiment 4 (carbon-fiber cross section: $7.85 \times 10^{-7}$ cm$^2$) as sectional area electrode, a saturated sodium chloride calomel electrode (SSCE) as a reference electrode and a platinum wire as an opposing electrode. A plot of current response at this time with respect to glucose concentration in the solution is shown in FIG. 13. A region of linear current response was obtained over a range of glucose concentration of 0-105 mg/dl. It was found that response time in this case is less than two seconds for a 95% response, which is indicative of a very high speed of response. The specimen solution was stirred gently with a stirrer at 25° C. and measured using a 5 mM phosphate buffer solution (pH: 6.2).

Embodiment 5

After an ultraminiature enzyme sensor was manufactured in the same manner as in Embodiment 4, a glucose-permeable film 18 (20 μm) was formed by repeatedly dipping the sensor in a dichloromethane solution of 5% cellulose acetate, and allowing it to dry, three times. The enzyme-fixed film preferably is 400 Å-50 μm, with 1-10 μm being particularly desirable. The enzyme is not fixed sufficiently and lifetime is short below 400 Å, and speed of response diminishes when 100 μm is exceeded.

Experiment 12

The subminiature enzyme sensor of Embodiment 5 was treated as in Experiment 9 and current response with respect to glucose concentration was investigated. As a result, it was found that the region of linear current covered a wide range of 0-240 mg/dl. It was found that speed of response in this case was less than three seconds for a 95% response, and that a slowing of the response due to the glucose-permeable film was small.

As described in detail above, the electrode area is ultraminiaturized in the enzyme sensor of the present embodiment. The following advantages are obtained as a result:

(1) Basic concentration measurement in a living body or tissue is possible.

(2) Measurement of trace amounts of a sample on the μl order is of course possible.

(3) Since the sensor substrate is ultraminiaturized, response is a very quick three seconds and rapid measurement is possible.

(4) Cost is low since inexpensive carbon fiber can be used.

(5) A change in concentration caused by reaction is negligible owing to the very small responsive area.

(6) The influence of solution fluidity and flow is negligible.

It should be noted that material other than a slender carbon material, such as a metal (e.g., gold) or metal oxide [iridium oxide, indium tin oxide (ITO)], may be used as the electrically conductive substrate.

Furthermore, though the film-coated sensors of these embodiments are typified by oxygen sensors and enzyme sensors, as stated at the beginning of the description of the embodiments, the present invention can be similarly applied to other film-coated sensors.

The embodiments can be modified, rearranged or altered without departing from the scope of the following claims.

What is claimed is:

1. A film-coated sensor comprising:
a capillary having two open ends;
an electrically conductive substrate having less than $10^{-5} cm^2$ cross-sectional area, being connected to a lead wire at one end and another end internally located at one open end of said capillary; and
a sensing film coating a surface of said another end of said electrically conductive substrate at said open end of said capillary for sensing a substance of interest contained in a biological fluid.

2. The film-coated sensor according to claim 1, wherein said electrically conductive substrate is at least one carbon fiber, a rod-shaped carbon, a gold wire or a metal oxide wire.

3. The film-coated sensor according to claim 1, wherein said sensing film comprises a reducing catalytic film for sensing a gas of interest and an enzyme film coating a surface of said reducing catalytic film for generating said gas of interest selectively in response to said substance of interest.

* * * * *

UNITED STATES PATENT AND TRADEMARK OFFICE
CERTIFICATE OF CORRECTION

PATENT NO. : 5,186,808

DATED : February 16, 1993

INVENTOR(S) : Shuichiro YAMAGUCHI et al

It is certified that error appears in the above-identified patent and that said Letters Patent is hereby corrected as shown below:

In Column 4, line 23, delete "6 m" and insert -- 6 um --.

In Column 7, line 30, after "1,", insert -- the relationship between the density of peak current and --.

In Column 12, line 30, after "said" and before "open", insert -- one --.

Signed and Sealed this

Sixteenth Day of November, 1993

Attest:

BRUCE LEHMAN

Attesting Officer     Commissioner of Patents and Trademarks